US006530924B1

(12) United States Patent
Ellman et al.

(10) Patent No.: US 6,530,924 B1
(45) Date of Patent: Mar. 11, 2003

(54) ELECTROSURGICAL TONSILAR AND ADENOID ELECTRODE

(76) Inventors: Alan G. Ellman, 1135 Railroad Ave., Hewlett, NY (US) 11557; Jon C. Garito, 1135 Railroad Ave., Hewlett, NY (US) 11557

( * ) Notice: Subject to any disclaimer, the term of this patent is extended or adjusted under 35 U.S.C. 154(b) by 101 days.

(21) Appl. No.: 09/705,195

(22) Filed: Nov. 3, 2000

(51) Int. Cl.⁷ .............................................. A61B 18/18
(52) U.S. Cl. ........................ 606/45; 606/41; 606/49
(58) Field of Search ..................... 606/41, 45, 46, 606/47, 48, 49, 50

(56) References Cited

U.S. PATENT DOCUMENTS

| | | | | |
|---|---|---|---|---|
| 5,261,905 A | * | 11/1993 | Doresey, III | 606/41 |
| 5,295,990 A | * | 3/1994 | Levin | 600/564 |
| 5,364,395 A | * | 11/1994 | West, Jr. | 604/22 |
| 5,482,054 A | * | 1/1996 | Slater et al. | 600/564 |
| 6,110,196 A | * | 8/2000 | Edwards | 606/32 |
| 6,126,656 A | * | 10/2000 | Billings | 606/41 |
| 6,159,207 A | * | 12/2000 | Yoon | 606/41 |
| 6,348,051 B1 | * | 2/2002 | Farin et al. | 606/37 |

* cited by examiner

Primary Examiner—Linda C. M. Dvorak
Assistant Examiner—Kenneth Schopfer

(57) ABSTRACT

A electrosurgical electrode specifically adapted for use in a surgical procedure for removing lymphoid tissue, specifically a tonsillectomy or adenoidectomy procedure. The electrosurgical electrode incorporates a suction or irrigation conduit in the form of a hollow tube for conveying the suction or fluid to the active electrode end. The electrosurgical electrode is preferably provided with a generally spoon-shaped body with a curved end comprising a wire or serrated active edge from which electrosurgical currents can emanate for dissection and hemostasis of tissue.

4 Claims, 3 Drawing Sheets

ELECTROSURGICAL TONSILAR AND ADENOID ELECTRODE

RELATED APPLICATION

Co-pending U.S. application, Ser. No. 09/693,176 filed Oct. 23, 2000, commonly owned, for "Suction Attachment For Electrosurgical Handpiece".

This invention relates to electrosurgery, and in particular to an electrode for attachment to an electrosurgical handpiece for use in electrosurgical procedures which tend to produce vapors, odors or smoke plumes or which may require irrigation.

BACKGROUND OF THE INVENTION

Electrosurgery is a common procedure for dentists, doctors, and veterinarians. Electrosurgical handpieces are commercially available that will accommodate a wide variety of electrodes shapes and sizes, such as needles, blades, scalpels, balls and wire loops. Also, multi-function electrodes are available. A suction coagulator is described in U.S. Pat. No. 5,196,007, whose contents are herein incorporated by reference. This is an instrument that can be connected to a source of electrosurgical energy and that provides the handpiece in the form of a hollow tube with an exposed tip. By connecting a suction source to the hollow tube end, blood and other liquids as well as vapors and odors at the operative field can be drawn out while simultaneously bleeding capillaries can be coagulated electrosurgically. This instrument is adapted to receive a suction hose at its rear, and it requires a special nosepiece to receive an electrical connector for supplying the active electrosurgical currents.

Clip-on suction attachments for electrosurgical pencil type handpieces are also available, but often the cost is high and/or the attachment detracts from the surgeon's ability to manipulate the handpiece with the clip-on attachment.

The importance of using suction to capture smoke and plume generated during an electrosurgical procedure is also well known in the art. Such procedures involving tissue excision invariably result in the generation of smoke and odors. This causes several problems. Firstly, the smoke interferes with the vision of the surgeon. Secondly, the smoke can be inhaled by the patient or the surgeon. Thirdly, the odors are offensive. See, for example, U.S. Pat. No. 6,001,077, which describes a plume evacuation system employing a novel wand—the fitting used to capture the plume and which is attached to the suction apparatus—whose contents are herein incorporated by reference. See also the copending related application, which describes a suction attachment for a standard electrosurgical pencil type handpiece which also allows the location of suction close to the active electrode end of a conventional electrosurgical electrode and whose contents are herein incorporated by reference.

Tonsillectomy is a very common surgical procedure in children and is frequently performed together with Adenoidectomy. Tonsillectomy in adults is not infrequent. It has become apparent that the tonsils, usually in association with the adenoids in children, and the uvulopalatal area in adults, may be a cause of snoring and sleep apnea. Traditionally, the Tonsillectomy is performed under general anesthesia, in a hospital setting, by dissecting the tonsil from its bed. Postoperatively, the vital signs are monitored so that any reactionary hemorrhage is quickly recognized. The patient is nursed in the coma position until the cough reflex has recovered. Reactionary hemorrhage, occurring within the first 24 hrs. of post-surgery, is the most lethal complication. Secondary hemorrhage is due to infective slough separating from the tonsil bed and occurs about 5–10 days post-surgery.

Electrocoagulation is a frequent method being used today to achieve hemostasis. Recently, a Bipolar Suction dissector was announced to address the dissection, coagulation and suction in the Tonsillectomy procedure. See U.S. Pat. No. 5,603,712. The Bipolar Suction dissector requires a pair of arms, which are joined by a connecting plug into a forceps orientation. One arm is a tubular suction channel; the other arm is fitted with a dissecting blade. Tissue must be clasped between the two arm pole ends to achieve bipolar coagulation. This device works well to achieve electro-bipolar coagulation; however both the bipolar and bipolar forceps design is a poor dissector/cutting device.

Another surgical device which attempts to simultaneously incise and coagulate tissue is the diathermy scalpel, which utilizes low frequency electrical current and a standard electrode needle. See Akkielah et al., Journal Of Laryngology and Otology, Aug. 1997, Pgs. 735–738. The disadvantages of this method are inadequate hemostasis and unwanted thermal tissue necrosis. The use of lasers to incise and coagulate tonsils has also been used although not satisfactorily. Surgeons are accustomed to the tactile feedback that traditional surgical scalpels provide and they are uncomfortable and reluctant to utilize a device which is held above and apart from the tissue. It is also very difficult to accurately position the laser wand and arm within the small oral cavity.

Tonsillectomy excisions have also been attempted using low frequency, high power electrosurgical devices combined with a stream of high temperature gases through the electrode and directed at the tissue, in order to form the incision and coagulate tissue. This method is problematic in that it exhibits slow excision rates and high thermal tissue necrosis. Furthermore, gas embolization has been reported following surgery with this electrosurgery gas interface.

SUMMARY OF THE INVENTION

An object of the invention is an electrosurgical electrode for removing lymphoid tissue that is capable of locating close to the operative field, i.e., the tissue being treated, a source of suction or irrigation.

A further object of the invention is a suction device for an electrosurgical handpiece that ensures that the active end from which the suction is active is located close to the operative field.

Another object of the invention is a unipolar electrosurgical electrode configured to carefully dissect the tonsil or the adenoid from its bed and capsule.

Still another object of the invention is a suction device for an electrosurgical handpiece that is capable of providing efficient smoke removal or irrigation and that is relatively inexpensive to manufacture.

Still a further object of the invention is a suction device integrated with an electrosurgical electrode specifically adapted for use in a tonsillectomy procedure.

According to one aspect of the invention, a suction/irrigation conduit is integrated into a unipolar electrode itself in such manner that the plume receiving or active suction or irrigation opening is not obstructed and is always as close as possible to the operative field. The opposite end of the conduit when used to provide suction is air-coupled to a suction source which can be the device of U.S. Pat. No.

5,196,007 which supplies the suction via the handpiece handle, or via the suction attachment described in the related copending application, and may even be a clip-on attachment. When used to provide irrigation, the opposite end of the conduit is fluid-coupled to a fluid source.

According to another aspect of the invention, the electrode is dish-shaped, preferably configured in the shape generally of a spoon, with the front end exposed to provide electrosurgical currents to the tissue. In a preferred embodiment of the invention, the electrode is configured for performing a tonsillectomy or adenoidectomy procedure in which the tonsils or adenoids of a patient are excised by means of an exposed curved wire or serrated edge to which electrosurgical voltages are applied. The suction/irrigation conduit is part of the electrode shank achieved by using a hollow tube as the shank. The suction opening is located close to the active curved wire or serrated edge. Preferably, the hollow tube is of metal of a standard size for mounting in standard electrosurgical handpieces, and the hollow tube is used to connect the curved wire or serrated edge to a cable connected to the electrosurgical apparatus.

The tonsillectomy or adenoidectomy procedure is often associated with a high level of pain and risk of bleeding in the post-operative period. The main purpose or intent in the tonsillectomy or adenoidectomy procedure using the electrosurgical electrode according to the invention is to dissect, namely, carefully and precisely cut out the tonsil or adenoids from its bed and capsule. The second most important point would be hemostasis control. The third important goal is to substantially reduce unwanted thermal tissue necrosis, by limiting the electrosurgical energy to remove only tonsillar or adenoidal tissue and prevent the electrosurgical energy from affecting the surrounding healthy tissue. A fourth important point of the procedure is to remove the smoke plume, which results from the dissection of the tonsil or adenoid. This actually accomplishes several important advantages. It visually clears the surgical sight for the surgeon. It prevents the plume from traveling to the nose and throat of the patient—smoke or plume is a larger problem when operating inside the oral or nasal passageways as the patient may inspire the potentially harmful smoke or plume. It draws cool air over the surgical sight. The electrode of the invention satisfies these four important aspects of the surgical procedure in a relatively simple and inexpensive manner. A further advantage is that the same suction port could easily be used to aspirate or flow water or other liquid to the tissue, to cool it down and create a moist wet setting.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF THE PREFERRED EMBODIMENTS

U.S. Pat. No. 6,001,077 shows a typical surgical smoke plume evacuation system with a hand-held wand connected via filters and a vacuum hose to a vacuum blower, referred to herein as the suction generator. U.S. Pat. No. 5,196,007 (the '007 patent) shows integration of a suction wand with a handpiece. This latter construction take advantage of the fact that the interior of the handpiece is hollow and can convey the suction pressure to the front of the handpiece. However, the handpiece is not a standard electrosurgical handpiece or electrosurgical pencil as it is often called, and the electrical connection must be made via a special fitting attached to a special nosepiece.

The invention described in the related copending application provides a suction attachment that can be attached directly to a standard handpiece and that can provide a source of suction or fluid at an opening at the distal end of the handpiece close to the active electrode end.

The invention described in the present application provides an electrode configuration that can be attached directly to the handpiece described in the '007 patent, to the suction attachment of the copending application, or to any similar handpiece or attachment that can provide a source of suction or fluid at an opening at the distal end of the handpiece or attachment close to the active electrode end.

Figure 1:
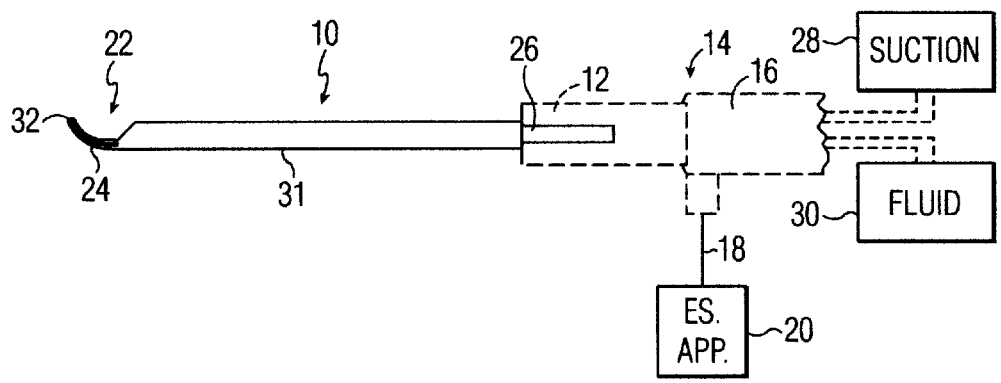
FIG. 1 is a side view of one form of electrosurgical electrode according to the invention shown attached to a schematic of the handpiece described in the '007 patent which is in turn electrically connected to electrosurgical apparatus and suction and fluid sources.
Figure 2:
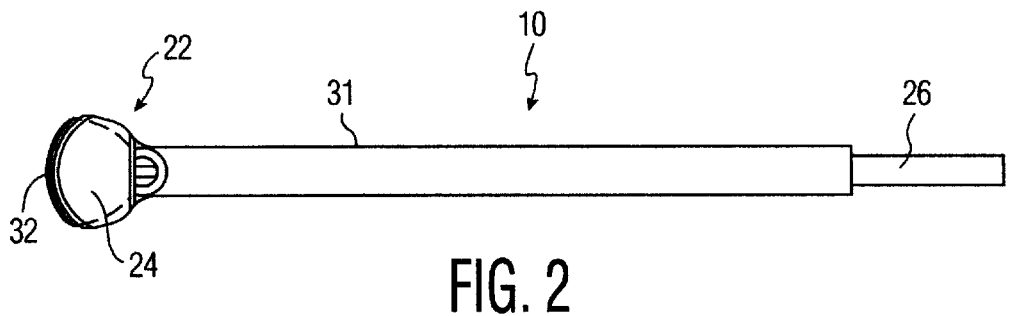
FIG. 2 is a top view of the electrosurgical electrode of FIG. 1.

FIG. 1 is a side view and FIG. 2 is a top view of a unipolar electrosurgical electrode 10 according to the invention attached to the nosepiece 12 of the hollow handpiece 14 described in the '007 patent. The latter comprises a handle 16 having at its side a cable 18 connected at its opposite end to a connector (not shown) for plugging into a standard electrosurgical apparatus 20 supplying electrosurgical currents to the electrode 10 having a working end 22 in the form generally of a spoon 24. Inside the nosepiece 12 is a collet (not shown) which receives the electrically-conductive shank 26 of the electrode for holding the electrode within the electrosurgical handpiece 14. The cable 18 is electrically connected to the collet which in turn is electrically connected to the electrode 10 so that when the electrosurgical apparatus 20 is switched on, electrosurgical currents are supplied to the electrode. It is also common for the handpiece handle to have switches (not shown) for remote operation of the electrosurgical apparatus. Also shown in FIG. 1 are sources of suction 28 and fluid 30 which may be selectively connected to the hollow handpiece 14 to supply suction or fluid, respectively, to the shank 26 of the electrode 10.

The electrosurgical apparatus preferably is an ultra high frequency (RF) radiosurgical energy source, which operates in the range of about 3.8–4.0 MHz. Studies have shown that the 3.8–4.0 MHz frequency range is the preferred RF energy to incise and coagulate tissue because tissue thermal necrosis is minimal and, when interfaced with the electrosurgical electrode of the invention, provides excellent cutting and hemostasis especially for tonsillectomy and adenoidectomy procedures. An example of suitable electrosurgical apparatus is the Model SURGITRON Dual-Frequency electrosurgical unit manufactured by and available from Ellman International, Inc. of Hewlett, New York.

Figure 3:
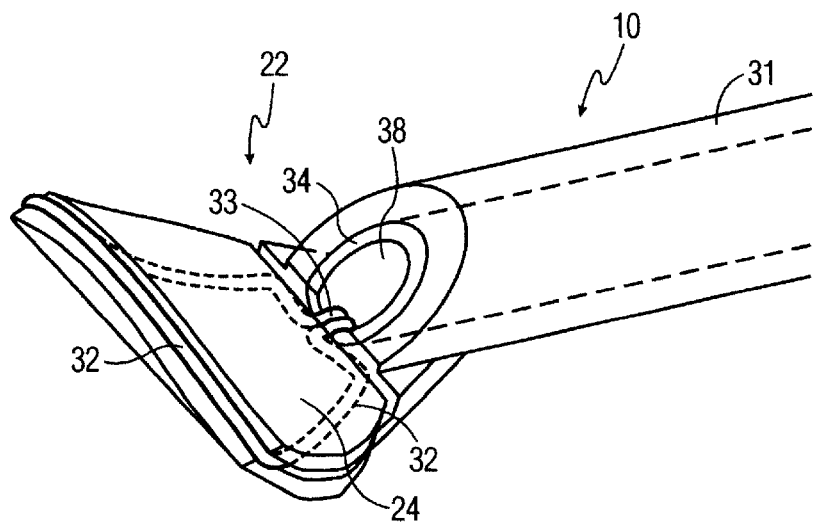
FIG. 3 is a perspective view of the front end of the electrosurgical electrode of FIG. 2.
Figure 4:
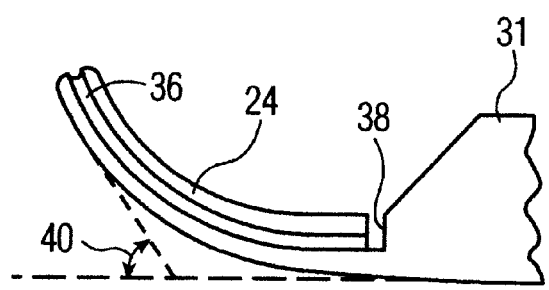
FIG. 4 is a side view of the electrosurgical electrode of FIG. 3 with the active wire removed.
Figure 5:
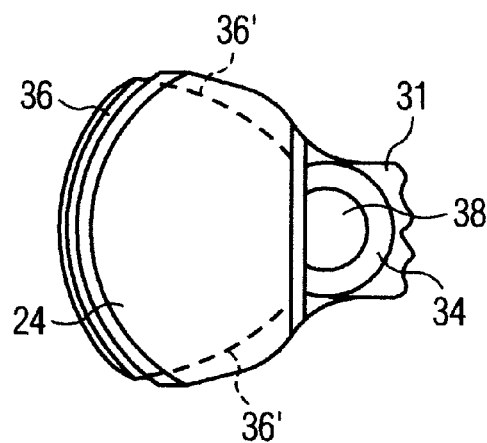
FIG. 5 is a top view of the electrosurgical electrode of FIG. 4.
Figure 6:
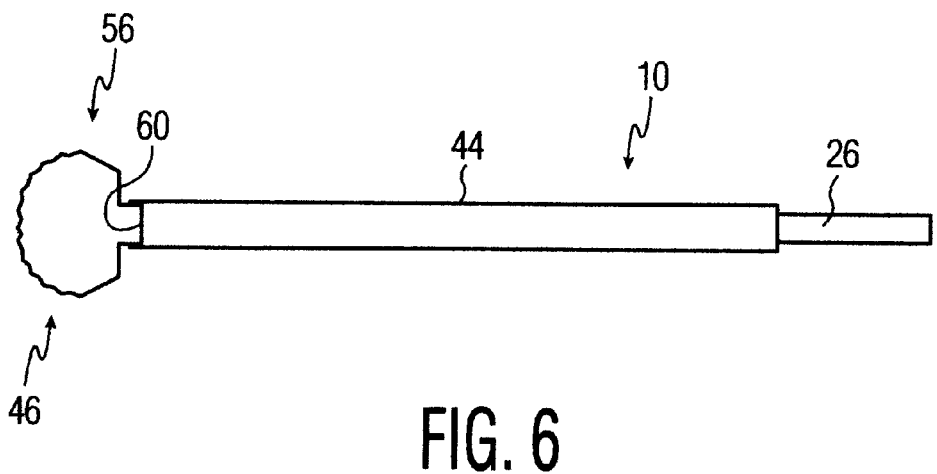
FIG. 6 is a top view of another form of electrosurgical electrode according to the invention.
Figure 7:
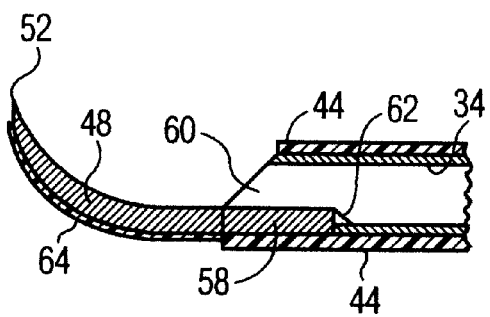
FIG. 7 is a cross-sectional view of the front end of the electrosurgical electrode of FIG. 6.
Figure 8:
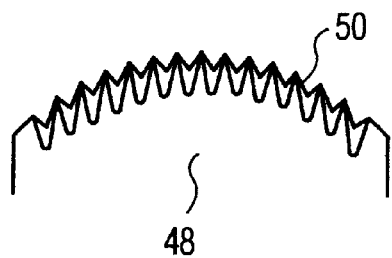
FIG. 8 is a enlarged view of the serrated end of the electrosurgical electrode of FIG. 6.
Figure 9:
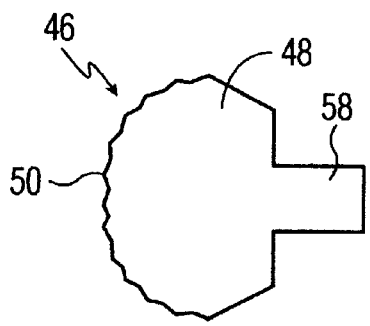
FIG. 9 is a top view of a variant of the electrosurgical electrode of FIG. 6.

FIG. 3 is a perspective view of the front working end 22 of the FIG. 1 embodiment. As can be seen more clearly in that figure, the spoon-shaped part 24 has an electrically-conductive wire loop 32 supported on the rim of the spoon 24 and projecting slightly forwardly (to the left in FIGS. 1–3) of the spoon. The wire 32 extends around the spoon periphery with only the front part of its outer surface exposed. The spoon is electrically-insulating, for example, of plastic. The electrode 10 has a straight body portion 31, which is also electrically-insulating, for example, of plastic, but which surrounds on its interior a metal (such as brass or other electrically-conductive material) hollow tube 34. The latter in turn forms the shank 26, which when mounted in the handpiece 14 is electrically connected to the cable 18. The construction may involve a plastic tube molded around the brass tube or a plastic tube heat-shrunk around the brass tube, leaving the shank 26 bare. Thus, the brass tube 34 is also electrically connectable to the electrosurgical apparatus 20. The electrically-conductive wire 32 extends around the periphery of the electrically-insulating spoon and its two ends connected as by welding 33 to the brass tube 34. The resultant electrode is thus a unipolar electrosurgical electrode. FIGS. 4 and 5 are side and top views of the electrically-insulating spoon 24 before installation of the active wire 32, which seats in a recess 36 at the front of the spoon 24 whose depth is chosen such that about half of the wire thickness extends out of the recess 36 in front. But, the recess 36' along both sides of the spoon (shown in dashed lines) is deeper than the wire thickness. As a result, the wire 32 is shielded within the electrically-insulating spoon 24. Consequently, all of the electrically-conductive parts of the electrode 10 are covered with electrically-insulating material except for the forward projecting part of the active wire 32.

In the operation of the system, with the suction source 28 attached to the handpiece 16, when the suction generator is activated, the reduced pressure is conveyed down the hollow handpiece 16, into and through the hollow brass tube 34, and escapes via the port 38 at the exit of the brass tube 34, which it will be noted is always located very close to the point of origin of the smoke plume, which is where the working electrode wire end 32 excises the tissue when the electrosurgical apparatus is activated. This allows smoke and airborne contaminants to be captured close to their point of origin, and avoids the need of an additional staff member to hold a separate plume capture device near the excision site. The close proximity of the capture port 38 to the plume origin also allows the use of lower reduced pressure and thus lower noise levels. Similarly, when the fluid source 30 is connected to the hollow handpiece and activated, fluid will exit from the port 38 again close to the excision site.

A typical length of the probe 10 is 6 inches long. When inserted into the handpiece 14, when the electrosurgical apparatus is activated and say the suction source activated, the electrode 10 provides both the suction and the high frequency RF energy. The probe 34 is preferably made of metal tubing, for example, of stainless steel, cobalt, tungsten, brass or nickel in diameter sizes of, for example, $\frac{1}{16}$ through $\frac{3}{32}$ inches, which will fit the typical nosepiece collet of a handpiece larger or smaller diameters are possible. The probe tubing 34 is electrically insulated by an appropriate insulating coating 31. The shank end of the probe is left with approximately 1½ inches of exposed metal for insertion and electrical connection to the handpiece, where it makes metal contact to provide RF energy to the exposed metal wire 32 at the opposite end. The exposed wire can be a bare single conductor wire with smooth sides or the outer side can be roughened or serrated to assist in concentrating the RF energy. The shaped working end further has a slight upward curvature of between 5° to 20°, indicated on FIG. 4 at 40. An angle of 15° is preferred. The lower end of the spoon-shaped active end meets the open end 38 of the tubing.

The curved spoon shape has a wide profile with a smooth electrically-insulated bottom which is manipulated by the surgeon such that the smooth bottom is guided by and follows along the plane of the walls of the soft palate, pharynx and tonsil capsule while the active projecting wire 32 is moved up against the tonsile base providing the complete electrosurgical extirpation and dissection of the full tonsil. An electrically insulated layer at the spoon bottom (which is the spoon bottom in this embodiment) and along the electrode body 31 protect from stray RF leakage energy that could burn unintended areas in the oral cavity. The tubing opening 38 integrates either suction or irrigation to the surgical site. The suction provides an escape of smoke, plume and secretions, which clears the surgical site for important visualization, and draws cooler air over the surgical site thus cooling down the surgerized tonsillar tissue and tonsil bed. The insulated spoon allows specific one-sided dissection and coagulation. The top side as shown is also protected by the plastic spoon top, but this is not essential because under normal usage, the top side of the spoon should never touch any tissue.

FIGS. 6–9 show a second embodiment of the invention. The hollow body 10 as before is made up of a hollow metal tube 34 coated, except at the shank end 26, with an electrically-insulating coating 44. However, in this case, the spoon 46 is a single spoon-shaped metal piece 48 (FIG. 9) whose front end is serrated 50 (not visible in FIG. 7, but shown in FIGS. 6 and 8). Like the spoon 22 in FIGS. 1–5, the spoon 48 curves upward at an angle of about 5°–20° (see FIG. 7). The radius along the top surface of the spoon part 48—preferably about 0.2–0.3 inches—is slightly larger than that of the bottom surface—preferably about 0.15–0.25 inches—with the result that the spoon tapers to a sharp edge 52 at its front surface. Preferably that front edge 52 is serrated into individual teeth having a short depth of about $\frac{1}{64}$–$\frac{1}{32}$ inches. The overall shape of the spoon 46 can be that shown in the variant of FIG. 9, or can be more rectangular as depicted at 56 in FIG. 6. For the latter, which is preferred, the number of teeth can vary between about 12–20 over a width of the front edge of about ¼–⅝ inches, preferably about ⅜ inches. A shank part designated 58 is welded 62 to the inside of the tube opening 60 from whence the suction or fluid emanates, which as before remains open and is positioned close to the excision site. The bottom and side edges of the spoon 46, 56 are preferably coated with a thin electrically-insulating layer 64, for example, of Teflon or ceramic, leaving the front teeth 50 uncoated and exposed. The top surface may also be coated if desired but need not be since under ordinary usage, it should not contact any patient tissue.

The spoon can be made of the same metals referenced above, and the serrations 50 can vary in coarseness and height of serration edges.

The relatively simple construction and the use of low-cost plastic or rubber parts in the manufacture of the electrode of the invention also has the advantage that the overall size and weight are low so that less of a strain is placed on the wrists or finger of the surgeon, which is important especially for delicate surgery, and thus the surgeon's tactile sense and dexterity need not be compromised. Manufacture is quite simple and low cost, which is important for disposable hospital and office environments. The connection of the suction attachment of the invention to the handpiece is simple and user-friendly.

The use of the serration teeth at the distal edge of the spoon-shaped working end provide several important advantages. The serration or teeth permit gentle exact scraping movements to cause a separation of the inferior side of the tonsil. What is important is that this can be done either mechanically without RF energy, or with RF energy being applied. When RF energy is supplied, it will flow to the sharp edges of the teeth at the front edge of the tonsil probe. The RF energy focuses on the fine edge points of the serrated edge of the probe tip. The RF energy flowing through the serrated edge of the spoon-shaped probe allows for dissection and excision of all degrees of vascular tonsil or adenoid tissue types, while at the same time effectively coagulating the tonsil bed. The insulated spoon allows specific one-sided dissection and coagulation.

An important feature is that suction is available while the tonsil is being extirpated from its bed. The suction port is ideally positioned within the spoon section of the RF tonsil probe. This enables the surgeon to move through the mucosal tissue and tonsil tissue with the RF tonsil probe cutting with both the serrated edge and RF energy flowing to the sharp serrated points, enhancing both the dissection of the mucosal tonsillar pillar and the tonsillar fibrous capsule from the muscular tonsillar bed, while simultaneously coagulating blood vessels. Simultaneously, suction can be operating, clearing the smoke plume and debris from the surgical field.

Another important feature is that the serrated edge and shape of the spoon-shaped probe becomes an excellent surgical tool for good blunt dissection, without RF energy being applied. This can be done by a back and forth motion while advancing the working edge, or by a simple pushing and shoveling action aganist the tonsil base.

Thus, the RF tonsil probe of the invention enables the surgeon to use one probe to provide the necessary surgical features of cutting, coagulation and suction, with or without suction or fluids, with RF energy being applied during part or all of the time that the dissection procedure is carried out, with RF energy and blunt dissection, or with blunt dissection, or with suction alone without RF energy being applied. The surgeon would be otherwise required to utilize several different surgical instruments to accomplish what the RF tonsil probe alone can accomplish. The changing of instruments during the surgical intervention prolongs the surgery, blood loss and anesthetic time for the patient.

By interfacing the RF tonsil probe with the ultra-high 3.8–4.0 MHz Radiosurgery apparatus, a number of surgical and clinical advantages, namely: better operative results, due to the high frequency radiosurgery device's ability to significantly reduce tissue necrosis; minimal scarring; reduced surgical pain and post-operative pain; and controlled bleeding and post-operative bleeding.

Other variations in the shape of the electrosurgical electrode working end while retaining its benefits and advantages will be evident to those skilled in the art.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical electrode comprising:
   a) an elongated body having first means at a first end for removably attaching to the nosepiece of an electrosurgical handpiece,
   b) said elongated body having second means at a second end providing an active electrosurgical end capable of supplying electrosurgical currents when the first means is connected to electrosurgical apparatus,
   c) said second means comprising a generally spoon-shaped body having along a front edge of its periphery, projecting forwardly of the spoon-shaped body in a direction away from the first end, an exposed electrically-conductive surface for contacting tissue and for delivering to the tissue electrosurgical currents when the first means is connected to electrosurgical apparatus,
   d) only the front edge being electrically-conductive and capable of delivering electrosurgical currents,
   e) wherein the electrode is a unipolar electrode and the spoon-shaped body has an upper side and a lower side and is solid and its lower side is coated with an electrically-insulating layer, the exposed surface along the front edge being free of the coating,
   f) the spoon-shaped body curving upward at an angle of about 5°–20°,
   g) the upper side of the spoon-shaped body having a first radius of curvature, the lower side of the spoon-shaped body having a second radius of curvature, and the first radius being slightly larger than the second radius such that the spoon-shaped body tapers to a sharp edge at its front edge.

2. An electrosurgical electrode as set forth in claim 1, wherein the first radius is about 0.2–0.3 inches, the second radius is about 0.15–0.25 inches, and the angle is 15°.

3. An electrosurgical electrode as set forth in claim 1, wherein the first means comprises a conduit for suction or irrigating fluid, the conduit having an opening over the upper side of the spoon-shaped body such that suction or fluid is directed toward the tissue when the electrically-conductive surface contacts the tissue.

4. An electrosurgical electrode comprising:
   a) an elongated body having first means at a first end for removably attaching to the nosepiece of an electrosurgical handpiece,
   b) said elongated body having second means at a second end providing an active electrosurgical end capable of supplying electrosurgical currents when the first means is connected to electrosurgical apparatus,
   c) said second means comprising a generally spoon-shaped body having along a front edge of its periphery, projecting forwardly of the spoon-shaped body in a direction away from the first end, an exposed electrically-conductive surface for contacting tissue and for delivering to the tissue electrosurgical currents when the first means is connected to electrosurgical apparatus, d) only the front edge being electrically-conductive and capable of delivering electrosurgical currents, e) wherein the electrode is a unipolar electrode and the spoon-shaped body has an upper side and a lower side and is solid and comprises electrically-insulating material and includes an exposed groove at its front and a buried groove along its sides, g) the spoon-shaped body curving upward at an angle of about 5°–20°, h) the active electrosurgical end being constituted by an electrically-conductive wire that is exposed and extends in the front groove and that continues into the buried grooves at the sides such that only the exposed wire in the front when activated can deliver to the tissue electrosurgical currents.

* * * * *